US005389374A

United States Patent [19]

Brown-Skrobot

[11] Patent Number: 5,389,374
[45] Date of Patent: Feb. 14, 1995

[54] PREVENTION OF TOXIN PRODUCTION USING ABSORBENT PRODUCTS

[75] Inventor: Susan K. Brown-Skrobot, Hamilton-Square, N.J.

[73] Assignee: McNeil-PPC, Inc., Milltown, N.J.

[21] Appl. No.: 128,336

[22] Filed: Sep. 29, 1993

Related U.S. Application Data

[63] Continuation of Ser. No. 936,689, Aug. 27, 1992, abandoned, which is a continuation of Ser. No. 695,471, May 3, 1991, abandoned, which is a continuation-in-part of Ser. No. 605,910, Oct. 30, 1990, abandoned.

[51] Int. Cl.[6] .......... A61F 13/02; A61F 13/15; A61F 13/20; A61L 15/16

[52] U.S. Cl. .......... 424/431; 424/404; 424/405; 424/411; 424/446; 604/360; 604/904

[58] Field of Search .......... 424/404, 405, 411, 431, 424/446; 604/360, 904

[56] References Cited

U.S. PATENT DOCUMENTS

| | | | |
|---|---|---|---|
| 3,052,607 | 9/1962 | Hirsh | 167/82 |
| 3,219,525 | 11/1965 | Berkow et al. | 167/58 |
| 3,584,119 | 6/1971 | Langley | 424/148 |
| 3,970,759 | 7/1976 | Frankenfeld et al. | 424/343 |
| 4,022,775 | 1/1977 | Kabara | 426/532 |
| 4,067,997 | 1/1978 | Kabara | 424/312 |
| 4,113,851 | 9/1978 | Leveen et al. | 424/28 |
| 4,347,237 | 8/1982 | Evenstad et al. | 424/78 |
| 4,374,522 | 2/1983 | Olevsky | 128/285 |
| 4,393,871 | 7/1983 | Vorhauer et al. | 609/58 |
| 4,405,323 | 9/1983 | Auerbach | 604/285 |
| 4,413,986 | 11/1983 | Jacobs | 604/14 |
| 4,431,427 | 2/1984 | Lefren et al. | 604/285 |
| 4,485,029 | 11/1984 | Kato et al. | 514/912 |
| 4,551,148 | 11/1985 | Riley et al. | 604/890 |
| 4,582,717 | 4/1986 | von Bittera et al. | 427/2 |
| 4,585,792 | 4/1986 | Jacob et al. | 514/474 |
| 4,722,936 | 2/1988 | Jacob | 514/474 |
| 4,722,937 | 2/1988 | Jacob et al. | 514/474 |
| 4,769,021 | 9/1988 | Kass | 604/367 |
| 4,788,060 | 11/1988 | Endicott et al. | 424/443 |
| 4,788,180 | 11/1988 | Bloch | 514/26 |
| 4,921,694 | 5/1990 | Hoppe et al. | 424/65 |
| 4,981,686 | 1/1991 | Hardy | 424/93 |
| 4,997,851 | 3/1991 | Isaacs et al. | 514/558 |
| 5,000,749 | 3/1991 | Le Veen et al. | 604/904 |

FOREIGN PATENT DOCUMENTS

| | | |
|---|---|---|
| 1123155 | 5/1982 | Canada . |
| 1192701 | 9/1985 | Canada . |
| 0117613 | 9/1984 | European Pat. Off. . |
| 0297310 | 1/1989 | European Pat. Off. . |
| 0302836 | 2/1989 | European Pat. Off. . |
| 522M | 5/1961 | France . |
| 1307930 | 8/1962 | France . |

(List continued on next page.)

OTHER PUBLICATIONS

EPO Search Report, Application No. 90108100.0, Mar. 19, 1991.
EPO Search Report, Application No. 91118543.7, Feb. 4, 1992.

(List continued on next page.)

*Primary Examiner*—D. Gabrielle Phelan
*Assistant Examiner*—Carlos Azpuru

[57] ABSTRACT

Absorbent products, especially catemenial tampons, for absorbing body fluids, such as menstrual fluid, blood and wound exudates, comprise an amount of a compound effective to inhibit the production of Enterotoxin A, Enterotoxin B and/or Enterotoxin C by *Staphylococcus aureus* bacteria when the products are brought into contact with the bacteria. The compositions of this invention are also useful to inhibit production of Streptococcal pyrogenic exotoxins A, B and C, as well as hemolysins produced by Groups A, B, F and G streptococci in solution as well as being expected to be effective to inhibit such toxin and hemolysin production when used in conjunction with absorbent products. The compound is selected from the group consisting of monoesters of a polyhydric aliphatic alcohol and a $C_8$–$C_{18}$ fatty acid; diesters of a polyhydric aliphatic alcohol and a $C_8$–$C_{18}$ fatty acid; and mixtures thereof. The monoesters and diesters have at least one hydroxyl group associated with their aliphatic alcohol residue.

9 Claims, No Drawings

FOREIGN PATENT DOCUMENTS

| | | |
|---|---|---|
| 3309530C1 | 10/1984 | Germany . |
| 115016 | 2/1957 | New Zealand . |
| 183977 | 4/1979 | New Zealand . |
| 191703 | 12/1981 | New Zealand . |
| 194821 | 12/1982 | New Zealand . |
| 198139 | 7/1985 | New Zealand . |
| 209843 | 3/1987 | New Zealand . |
| 210484 | 5/1988 | New Zealand . |
| 221168 | 8/1989 | New Zealand . |
| 222761 | 10/1989 | New Zealand . |
| 219973 | 5/1990 | New Zealand . |
| 1374105 | 11/1974 | United Kingdom . |
| 2107192 | 4/1983 | United Kingdom ............. 604/904 |
| WO86/05388 | 9/1986 | WIPO . |

OTHER PUBLICATIONS

EPO Search Report, Application No. 91118572.6, Feb. 10, 1992.

Altenbern, *Protease Inhibitors Suppress Enterotoxin B Formation By Staphylococcus Aureus*, FEMS Microbiology Letters 3 (1978) pp. 199–202.

Ansari et al., *Sodium Bicarbonate Sodium Bicarbonate Douchng for Improvement of the Postcoital Test*, Fertility and Sterility, vol. 33, No. 6, (Jun. 1980) pp. 608–612.

Flournoy et al., *The Role of Lauricidin as an Antimicrobial Agent*, Drugs of Today, vol. 21, No. 8, (1985) pp. 373–377.

Gossel, *Feminine Hygiene Products: Why Your Advice is Needed*, U.S. Pharmacist, (May 1986), pp. 20–27.

Iandolo, *Genetic Analysis of Extravellular Toxins of Staphylococcus Aureus*, Annu. Rev. Microbiol. (1989) 43: pp. 375–402.

Iandolo et al., *Regulation of Staphylococcal Enterotoxin $B^1$, Infection and Immunity*, vol. 16, No. 2 (May 1977), pp. 610–616.

Ibrahim et al., *Inhibition of Growth of Staphylococcus Aureus and Enterotoxin–A Production in Cheddar Cheese Prod. with Induced Starter Failure*, J. of Food Protec. vol. 44, No. 3, (Mar. 1981) pp. 189–193.

Kabara, *Structure-function Relationships of Surfactants as Antimicrobial Agents*, J. Soc. Cosmet. Chem., vol. 29, (Nov. 1978), pp. 733–741.

Notermans et al, *Effect of Glyceryl Monolaurate on Toxin Production by Clostridium Botulinum in Meat Slurry*, J. of Food Safety vol. 3, (1981), pp. 83–88.

Orden et al., *Detect. of Staph. Enterotoxin and Toxic Shock Synd. Toxin–1 (TSST–1) by Immunoblot Comb. with a Semiautomated Electrophoresis System*, J. of Immuno. Meth. vol. 144, pp. 197–202 (1991).

Reiser et al., *Prod. of Toxic Shock Synd. Toxin 1 by Staph. aureus Restricted to Endogenous Air in Tampons*, J. of Cl. Microb., vol. 25, No. 8, (Aug. 1987), pp. 1450–1452.

Robbins et al., *Produc. of Toxic Shock Synd. Toxin 1 by Staphy. aureus as Determined by Tampon Disk–Membrane–Agar Method*, J. of Clin. Microbio., vol. 25, No. 8, (Aug. 1987), pp. 1446–1449.

Schlivert, *Staphy. Enterotoxi B and Toxic–Shock Synd. Toxin–1 are Significantly Assoc. with Non–Menstrual TSS*, The Lancet, May 17, 1986, vol. 1, pp. 1149–1150, (Abstract).

Schlivert et al., *Toxic Shock Synd. Staphylococcus Aureus: Effect of Tampons on Toxic Shock Synd. Toxin 1 Production*, Obstetrics & Gynecology, vol. 64, No. 5 (Nov. 1984), pp. 666–671.

Smith et al., *Enterotoxin A Synthesis in Staphylococcus aureus: Inhibition by Glycerol and Maltose*, J. of Gen. Microbiology, (1986), 132, pp. 3375–3380.

Smith et al., *Effect of Glucose Analogs on the Synthesis of Staphylococcal Enterotoxin A*, Journal of Food Safety 8, (1987), pp. 139–146.

Strobino et al, *Exposure to Contraceptive Creams, jellies and Douches and their Effect on the Zygote*, Society for Epidemiologic Research: Abstracts, p. 434.

Tierno et al., *In vitro Amplification of Toxic Shock Syndrome Toxin–1 by Intravaginal Devices*, Contraception, vol. 31, No. 2 (Feb. 1985), pp. 185–194.

Garbe, et al., *Staphy. aureus Isolates from Patients with Nonmenstrual Toxic Shock Synd.*, JAMA, May 3, 1985, 253 (17) pp. 2538–2542.

Humphreys, et al., *Enterotoxin Production by Staphy. aureus Isolates from Cases of Septicaemia and from Healthy Carriers*, J. Med. Microbiology, Mar. 1989, 28, (3) pp. 163–172.

Crass, et al., *Involvement of Staphy. Enterotoxins in Nonmenstrual Toxic Shock Synd.*, J. Clin. Microbiol., Jun. 1986, 23, (6), pp. 1138–1139.

PREVENTION OF TOXIN PRODUCTION USING ABSORBENT PRODUCTS

This is a continuation, of application Ser. No. 936,689, filed Aug. 27, 1992, now abandoned, which is a continuation of application Ser. No. 695,471, filed May 3, 1991, now abandoned, which is a C-I-P of application Ser. No. 07/605,910, filed Oct. 30, 1990, now abandoned.

FIELD OF THE INVENTION

This invention relates to absorbent products and especially to absorbent products such as tampons, sanitary napkins, wound dressings, nasal packing and the like which are adapted to absorb body fluids like menstrual fluid, blood and wound exudates. More particularly, the invention relates to the addition of active compounds which, when exposed to bacteria in absorbent products, will reduce the amount of toxins produced by bacteria coming into contact with them.

BACKGROUND OF THE INVENTION

The staphylococcal enterotoxins are extracellular proteins composed of sinule polypeptide chains of about 30 kd that characteristically have a disulfide loop near the middle of the molecule. They are categorized into five serological groups, designated Staphylococcal enterotoxin A (SEA), Staphylococcal enterotoxin B (SEB), Staphylococcal enterotoxin C (SEC), Staphylococcal enterotoxin D (SED) and Staphylococcal enterotoxin E (SEE). Based on differences in minor epitopes, SEC has been further subdivided into three types designated $SEC_1$, $SEC_2$ and $SEC_3$. A sixth group, SEF, was also described and was implicated as the causative agent of toxic shock syndrome. It has since been discounted as an enterotoxin and renamed toxic shock syndrome toxin-1 (TSST-1), as cited by J. J. Iandolo in Ann. Rev. of Micro. Vol. 43, pp. 275-402, 1989.

Menstrually occurring toxic shock syndrome is a severe and sometimes fatal multi-system disease associated with infection or colonization by *Staphylococcus aureus* (*S. aureus*) bacteria, has been linked to the use of tampons during menstruation. In Toxic shock syndrome(TSS), whether associated with menstruation or not, the symptoms include fever, hypotension, rash, and desquamation of the skin. TSST-1 is highly associated with menstrual cases but is less often isolated from *Staphylococcus aureus* strains in non-menstrual cases of the illness. Since TSST-1 can induce many clinical features of TSS in the rabbit and other species, it is generally thought to be the causative toxin in TSS (Schlievert, "Staphylococcal Enterotoxin B and Toxic Shock Syndrome Toxin-1 Are Significantly Associated With Non-menstrual TSS", The Lancet, Vol. 1(8490), May 17, 1986, p.1149). However, Garbe (Garbe P. L., Arko R. J., Reingold A. L., et al. "*Staphylococcus aureus* isolates from patients with non-menstrual toxic shock syndrome: Evidence for additional toxins", JAMA 1985; Vol 253; pp. 2538-42) noted that many TSS isolates from nonmenstrual cases did not express TSST-1 though they did cause TSS-like symptoms in a rabbit model. Of the toxins formed by *S. aureus* nonmenstrual isolates, TSST-1 was produced by 40% of those reported by Schlievert, 1986. Further, enterotoxin B was made by 38% of all non-menstrual TSS strains. Furthermore, Schlievert reported about 78% of non-menstrual TSS or probable TSS isolates expressed either TSST-1 or enterotoxin B compared with 20% of non-menstrual non-TSS isolates ($p < 0.001$).

Isolates from thirty patients suffering from confirmed or probable toxic shock syndrome were also examined for enterotoxins and exfoliative toxins. It was found that enterotoxin B was made by 38% of all nonmenstrual TSS strains. Crass and Bergdoll, 1986 reported a total of 46 (83.6%) of 55 *S. aureus* isolates produced TSST-1: 12 (25.5%) alone, 21 (46.8%) with Staphylococcal Enterotoxin A and 13 (27.7%) with Staphylococcal Enterotoxin C. Eight of the *S. aureus* isolates that did not produce TSST-1 did produce Staphylococcal enterotoxin B.

Humphreys (1989) reported the studies of *S. aureus* isolates obtained from cases of septicaemia, in which 33 (63%) produced enterotoxins A, B, C, or D alone or in combination.

Toxic shock syndrome toxin 1 (TSST-1) is classified as a member of the pyrogenic exotoxin-staphylococcal enterotoxin group of toxins on the basis of a patient's symptoms. However, TSST-1 and its cognate antiserum do not cross-react with any of the sera or proteins of other members of this toxin family. Furthermore, TSST-1 lacks the cysteine loop present in the remaining members of the toxin family, an important structural feature of this family of toxins. TSST-1 has very little amino acid homology with other members of this toxin family. The lack of a close sequence relationship between TSST-1 and other toxins may suggest that it is more closely related to the ancestral progenitor of this family or, alternatively, is wrongly included in this group of toxins (Iandolo, 1989). Nevertheless, TSST-1 bears little structural relationship to the other members of the pyrogenic exotoxin-staphylococcal enterotoxin group (Iandolo, 1989).

Subsequent to the publication of reports associating toxic shock syndrome with the use of tampons, a number of investigators undertook studies designed to evaluate the effect of tampons on growth of *S. aureus* bacteria as well as the effect of tampons on the production of TSST-1 by that bacteria. Early efforts to elucidate the role of tampons in TSS yielded conflicting data. Schlievert et al. (Obstet. Gynecol., Vol. 64, pp. 666-670, November 1984) studied the effect of tampons on *S. aureus* to evaluate whether or not tampon components increase growth of *S. aureus* and production of toxic shock syndrome toxin-1. It was concluded that, under the test conditions of their study, tampon components provide neither nutrients for growth of toxic shock syndrome *S. aureus* nor factors that induce production of toxic shock syndrome toxin-1 above control levels. After six-hours' incubation, some commercially available tampons which were tested were inhibitory to bacterial growth and suppressed toxin production. Others suppressed toxin production but did not inhibit cell growth. One tampon inhibited cell growth but increased the amount of toxin produced. On the other hand, Tierno and Hanna (Contraception, Vol. 31, pp 185-194, 1985) reported that in their experiments tampons did stimulate *S. aureus* to produce TSST-1.

Reiser et al. (J. Clin. Microbiol., Vol. 25, No. 8, pp. 1450-1452, August 1987) thereafter reported the results of tests they conducted to determine the effect of four brands of tampons on production of toxic shock syndrome toxin-1. The amount of air available to the tampons which were tested was limited to that contained in sacs (made from cellulose sausage casing with a molecular weight cut-off of less than 10,000) in which the tampons were enclosed during testing. This method was deemed advantageous in that the limited amount of available air was thought to mimic more closely than previously used methods the in vivo condition in the vagina during menstruation with a tampon in place and in that the tampons which were tested were not altered prior to testing. The results of the tests conducted by Reiser et al. indicated that tampons provide increased surface area for the *S. aureus* bacteria to grow and adequate oxygen for toxin production. No significant inhibition of growth of the staphylococci bacteria or TSST-1 production by any of the tampons tested was noted.

Robbins et al., publishing in J. Clinical Microbiol., Vol. 25, No. 8, pp. 1446–1449, August 1987 at the same time as Reiser et al., reported the effect of 17 commercially available tampons on TSST-1 toxin production using a disk-membrane-agar (DMA) method, with incubation at 37° C. for 19 hours under 5% $CO_2$ in air. Filter membranes overlaying agar medium (with or without blood) in small petri dishes were spread inoculated with a TSST-1 producing strain of *S. aureus*. Robbins et al. concluded that the main role of tampons in TSS may be that of providing a fibrous surface for heavy colonization and sufficient air for TSST-1 production. In addition, they found evidence of inhibition of TSST-1 production by additives such as the deodorant/surfactant used in a commercially available deodorant tampon and a decrease in TSST-1 production by inhibiting growth of *S. aureus* as was observed in the case of a different commercially available tampon. It was thought that both inhibition of TSST-1 production and inhibition of *S. aureus* growth might prove to be important in reducing the risk of TSS.

U.S. Pat. No. 4,405,323 to Auerbach discloses a tampon designed to eliminate the hazards of toxic shock syndrome and dysmenorrhea. The tampon has incorporated therein an antibacterial agent which is said to disperse on contact with body fluids and prevent development of the organisms which produce the toxins which cause toxic shock syndrome. Among the antibacterial materials disclosed for use are povidone-iodine compound, mercury, zinc, penicillin, erythromycin and nitrofurazone.

Patent Cooperation Treaty Publication No. WO 86/05388 (published Sept. 25, 1986) to Kass teaches that the inclusion of a salt of a nontoxic divalent cation in absorptive pads, e.g. catemenial tampons, inhibits production of toxic shock syndrome toxin-1 and other staphylococcal products during use of said absorptive pad. Suitable salts include those of magnesium, barium, calcium or strontium (preferred) or of other divalent cations such as zinc, manganese, copper, iron, nickel and the like. The anionic portion of the salt is not critical. Magnesium stearate and magnesium acetate are particularly preferred salts for use in the invention.

U.S. Pat. No. 4,374,522 to Olevsky states that patterns of use of catemenial tampon seem to indicate that high absorptive capacity with the concomitant extended period of use of certain tampons are factors which contribute to the formation of toxic shock syndrome. The invention theorizes that tampons having limited absorptive capacity and requiring relatively more frequent changes may be desirable. The Olevsky patent provides a tampon made of conventional cellulosic materials, such as rayon fibers, which have been compressed into a bullet-shape with an open bottom surface sealed by a fluid impermeable sheet. The fluid impermeable bottom and the traditional bullet shaped pledget define a hollow core central reservoir area which is said to serve as a reservoir for excess menstrual fluid.

U.S. Pat. No. 4,431,427 to Lefren et al. discloses menstrual tampons comprising physiologically safe, water-soluble acids in their monomeric, oligomeric or polymeric forms. Citric, glycolic, malic, tartaric and lactic acids are disclosed as being useful in the practice of the invention. The presence of one or more of the above-noted acids in a tampon is said to inhibit the growth of bacteria responsible for toxic shock. Where an acid is used in its polymeric form, the tampon may additionally include an enzyme to hydrolyze the polymeric acid to its monomeric form.

Canadian Patent No. 1,123,155 to Sipos discloses a catemenial tampon for preventing toxic shock syndrome during menstrual flow. The body of the tampon, which is open at the insertion end and is closed at the withdrawal end, is snugly surrounded in its expanded condition by a fluid proof, thin and flexible membrane. This membrane, which can be made of polyethylene sheet, is biased against the vaginal wall during use of the tampon, is neutral to the vaginal mucosa and is completely impermeable to bacteria, viruses and toxic decomposition products of the menstrual flow.

Canadian Patent No. 1,192,701 to Bardhan discloses a tampon for the absorption of menstrual flow and comprising an inner layer of liquid-absorbent material and an outer layer which surrounds and encloses the inner layer. Menstrual discharge may flow inwardly to the inner layer but the outer layer is impervious to the passage of menstrual fluid outwardly from the inner layer. A plurality of liquid absorbent wicks extending from the inner layer through apertures formed in the outer layer serve as conduits for the flow of menstrual discharge from outside the tampon to the inner layer thereof. The disclosed structure is said to minimize the availability of discharge outside the tampon with a resulting reduction in the likelihood of growth of *S. aureus* and consequently its production of toxin. This patent also discloses that an antimicrobial compound which is bactericidal or bacteriostatic to *S. aureus* may be included in the inner layer. The antimicrobial agent may take the form of an antibiotic (such as penicillin, erythromycin, tetracycline or neomycin), a chemotherapeutic agent (such as a sulfonamide) or a disinfectant (such as phenol). The patent states that because the tampon is protected by its outer layer from contact with the vaginal wall, the risk of an allergic or other adverse reaction to the anti-microbial agent is minimized, and since the antimicrobial agent is also protected by the outer layer from contact with menstrual discharge, there is little risk of the destruction of commensal organisms in the vagina or development of resistance to the antimicrobial agent by *S. aureus* in any menstrual discharge outside the vagina.

S. Notermans et al. (Journal of Food Safety, Vol. 3 (1981), pages 83–88) reported that glyceryl monolaurate, when used in the proportion of 5g per kg. of meat slurry (pH 6.0–6.2) inhibited toxin productions by *Clostridium botulinum* type A, type B and type E. This article does not mention *Staphylococcus aureus* nor any toxins produced therefrom nor does it mention absorbent products or toxic shock syndrome.

U.S. Pat. No. 4,585,792 to Jacob et al. discloses that L-ascorbic acid when topically applied to the vaginal area of a human female during menses will inactivate toxins known to contribute to Toxic Shock Syndrome. The ascorbic acid compound may be carried by a vaginal tampon. The disclosure of U.S. Pat. No. 4,722,937, is to the same effect.

U.S. Pat. No. 4,413,986 to Jacobs discloses a tampon assembly packaged for sterile insertion of a tampon into the vagina having a guide tube telescoped around an insertion tube and a flexible sheath attached to the inner end of the guide tube and tucked into the inner end of the insertion tube. In use, as the insertion tube is pushed through the guide tube and into the vagina, the flexible sheath is pulled over the inner end of the insertion tube and extends along the exterior thereof. The portion of the insertion tube which is inserted into the vagina is at all times fully sheathed by the flexible sheath.

In tampon-associated toxic shock syndrome cases, the predominant toxin produced by *S. aureus* is toxic shock syndrome toxin-1 (TSST-1), while to a lesser extent, other enterotoxins can be produced. These non-TSST-1 enterotoxins are principally associated with nonmenstrual toxic shock syndrome.

There are compounds known to affect enterotoxin production. J. L. Smith, M. M. Bencievengo, R. L. Buchanan, and C. A. Kunsch reported, in an article entitled "Effect of Glucose Analogs on the Synthesis of Staphylococcal Enterotoxin A", Journal of Food Safety 8 (198) pp. 139–146 that glucose, 2-deoxyglucose and alpha-methyl glucose inhibited staphylococcal enterotoxin A synthesis by *Staphylococcus aureus* 196E, whereas beta-methyl glucose and 3-0-methyl glucose did not inhibit synthesis even at high concentrations. The formation of enterotoxins A and B is inhibited by glucose, with the extent of inhibition being strongly influenced by pregrowth of the bacteria in a glucose-containing medium as cited by Smith et al.

Iandolo and Shafer reported the effect of glucose and glucose analogs 2-deoxyglucose and alpha methyl glucoside on the synthesis and regulation of Staphylococcal enterotoxin B production (Iandolo and Shafer, "Regulation of Staphylococcal Enterotoxin B", Infection and Immunity, May 1977, pp. 610–615). The attenuating effect of glucose on Staphylococcal enterotoxin B was observed. However, when this effect was examined with analogs of glucose, contradictory responses were seen. Acid production due to glucose metabolism has been shown to reduce toxin production.

Ibrahim, Radford, Baldock and Ireland reported data indicating that, in cheese without starter activity, inhibition of growth of *S. aureus* and enterotoxin production may be achieved during production by not salting the curd at the end of cheddaring, avoiding pressing at high ambient temperatures and minimizing the pressing time of the curd (Ibrahim, et al., "Inhibition of Growth of *Staphylococcus aureus* and Enterotoxin-A Production in Cheddar Cheese Produced with Induced Starter Failure", Journal of Food Protection, Vol. 44, No. 3, pp. 189–193, March 1981). The authors also reported that storage of salted cheese at 11° C. appears to be a potential hazard because of significant increases in *S. aureus* count and entertoxin concentration. Surprisingly, the authors reported that the count of *S. aureus* decreased with no change in enterotoxin concentration in unsalted cheese stored at 11° C.

Another study was reported by J. L. Smith, M. M. Bencivengo and C. A. Kunsch that indicated that prior growth of *Staphylococcus aureus* 196E on glycerol or maltose led to cells with repressed ability to produce staphylococcal enterotoxin A (J. L. Smith et al., "Entertoxin A Synthesis in *Staphylococcus aureus*: Inhibition by Glycerol and Maltose", Journal of General Microbiology, Vol 132, pp. 3375–3380, 1986).

Chloramphenicol has also been reported as totally inhibiting Staphylococcal enterotoxin B production (Robert A. Altenbern, "Protease Inhibitors Suppress Enterotoxin B Formation by *Staphylococcus aureus*", FEMS Microbiology Letters, Vol. 3, pp. 199–202, 1978).

The production of TSST-1 by *S. aureus* has predominantly been associated with menstrual toxic shock syndrome, which has in turn been related to tampon usage. Unexpectedly, a group of compounds were identified which are effective to substantially reduce toxic shock syndrome toxin 1 production by *S. aureus* in vitro and in vivo. These compounds and the method of their use in absorbent products are described in copending U.S. patent applications Ser. No. 343,965 filed Apr. 27, 1989 and Ser. No. 316,742 filed Apr. 27, 1990.

However, despite the effectiveness of the compounds in inhibiting the production of TSST-1 toxin, there is no basis for predicting whether such compounds would be effective against SEA, SEB, and SEC production due to the structural and chemical differences between the TSST-1 toxin and other Staphylococcal enterotoxins.

SUMMARY OF THE INVENTION

Unexpectedly, it has been found that an absorbent product containing a compound selected from the group consisting of:

a) a monoester of a polyhydric aliphatic alcohol and a fatty acid containing from eight to eighteen carbon atoms and wherein said monoester has at least one hydroxyl group associated with its aliphatic alcohol residue;

b) diesters of a polyhydric aliphatic alcohol and a fatty acid containing from eight to eighteen carbon atoms and wherein said diester has at least one hydroxyl group associated with its aliphatic alcohol residue; and c) mixtures of the aforesaid monoesters and diesters reduces the amount of enterotoxins A, B, C and TSST-1 with enterotoxin A produced in vitro when said absorbent product is exposed to *Staphylococcus aureus* bacteria.

The fatty acid portion of the aforementioned monoesters and diesters may be derived from caprylic, captic, lauric, myristic, palmitic and stearic acids, which are saturated fatty acids whose chain lengths, respectively, are $C_8$, $C_{10}$, $C_{12}$, $C_{14}$, $C_{16}$ and $C_{18}$. The fatty acid portion of the aforementioned monoesters and diesters may be derived as well from unsaturated fatty acids having carbon chain lengths also ranging from $C_8$ to $C_{18}$, one example of such an unsaturated fatty acid being oleic acid. The preferred fatty acid for use in the practice of the present invention is lauric acid, a saturated fatty acid whose chemical formula is $C_{11}H_{23}COOH$.

As used in this specification and the appended claims, the term "aliphatic" has the meaning usually accorded it in organic chemistry, i.e. "aliphatic" refers to organic compounds characterized by straight—or branched—chain arrangement of the constituent carbon atoms.

As used in this specification and the appended claims, the term "polyhydric" refers to the presence in a chemical compound of at least two hydroxyl (OH) groups. Thus, a polyhydric aliphatic alcohol is one which has at least two hydroxyl groups and in which the carbon backbone is either straight or branched.

Polyhydric alcohols suitable for forming monoesters and/or diesters for use in the practice of the present invention are 1,2-ethanediol; 1,2,3-propanetriol (glycerol); 1,3-propanediol; 1,4-butanediol; 1,2,4-butanetriol and the like. The preferred polyhydric aliphatic alcohol for forming monoesters and diesters for use in the practice of the present invention is 1,2,3-propanetriol (commonly called glycerol) whose formula is $HOCH_2CH(OH)CH_2OH$.

It will be observed that the esters which are useful in the practice of the present invention have at least one hydroxyl group associated with their aliphatic alcohol residue. Thus, it will be understood that the monoester of 1,2-ethanediol and one of the aforementioned fatty acids may be used in the practice of the present invention because said ester, whose general formula is $$C_nH_{2n+1}-C(=O)-O-CH_2-CH_2OH$$

has at least one hydroxyl group (i.e. the hydroxyl group at the far right-hand side of the structural formula shown above) in that portion of the ester derived from the aliphatic alcohol 1,2-ethanediol. On the other hand, it will be understood that the diester of 1,2-ethanediol and one of the aforementioned fatty acids cannot be used in the practice of the present invention because said ester, whose general formula is $$C_nH_{2n+1}-C(=O)-O-CH_2-CH_2O-C(=O)-C_nH_{2n+1}$$

does not have at least one hydroxyl group in that portion of the ester derived from the 1,2-ethanediol.

The monoester of glycerol and one of the designated fatty acids may be used in the practice of the present invention because that ester will have two hydroxyl groups associated therewith which are derived from the glycerol. The diester of glycerol and one of the designated fatty acids may also be used because that ester will have one hydroxyl group associated therewith which is derived from the aliphatic alcohol glycerol. Indeed, as will be seen hereinafter, blends of glyceryl monolaurate and glycerol dilaurate have been found to be useful in the practice of the present invention. Finally, it will be understood that the triester of glycerol and one of the designated fatty acids cannot be used in the practice of the present invention because that ester does not have at least one hydroxyl group in that portion thereof which is derived from the aliphatic alcohol, i.e. glycerol.

Preferred esters for use in the practice of the present invention are glyceryl monolaurate, glyceryl dilaurate and mixtures thereof.

Other preferred esters for use in accordance with this invention include monolaurate derivatives of C-3 alkanols, such as 2-hydroxy-1-propyl laurate and 3-hydroxy-1-propyl laurate. Dilaurate derivatives of C-3 alkanols such as glycerol-1, 3-dilaurate, glycerol-1,2-dilaurate are also expected to reduce the amount of enterotoxins A, B, C and TSST-1 with Enterotoxin A produced. Ethylene glycol derivatives such as ethylene glycol monolaurate as well as polyethlyene glycol laurates, e.g., diethylene glycol monolaurate and triethylene glycol monolaurate are also expected to be active. Certain polymers are also expected to have toxin-reducing activity, for example, polyethylene glycol (200 MW) monolaurate, polyethylene glycol (400 MW) monolaurate, polyethylene glycol (1000 MW) monolaurate, and polypropylene glycol laurates such as polypropylene glycol monolaurate.

In accordance with the invention, the absorbent product contains an amount of the above-described ester which is effective to inhibit the formation of enterotoxins A, B, C and TSST-1 with enterotoxin A when said product is exposed to S. aureus. For example, effective amounts have been found to be from about 0.1% and higher of the specified mono- or diester compound (or mixtures thereof), based on the weight of the absorbent material comprising the absorbent product.

Preferably, the active ingredient contains at least 90% by weight of glyceryl monolaurate. More preferably, the active ingredient contains at least 95% by weight of glyceryl monolaurate. Most preferably, the active ingredient is substantially completely composed of glyceryl monolaurate.

Some similarity between toxins can be noted. The Streptococcal pyogenes exotoxin A (SPEA) is more closely related to the Staphylococcal enterotoxins. SPEA possesses a cysteine loop of nine amino acids similar to that of Staphylococcal enterotoxin A (SEA) and is also encoded by a converting phage. However, SPEA shares greater amino acid sequence similarity with Staphylococcal enterotoxin B than with SEA. Immunological studies have shown that the proteins and antisera to either enterotoxin are cross-reactive (Iandolo, 1989). These similarities between Staphylococcal enterotoxins A and B and the Streptococcal exotoxin A in both structure and reactivity lead to the hypothesis that the demonstration of an effect, such as reduction in enterotoxins A and B produced by Staphylococcus would translate to a similar effect on Streptococcal exotoxins. Glycerol monolaurate has been found to be effective in reducing the production of SPEA and SPEB in vitro using the tampon sac method.

As used herein, the term "absorbent material" includes natural or synthetic fibers, films, foams, wood pulp, peat moss, superabsorbent polymers and the like which are capable, either inherently or by virtue of the manner in which they have been assembled, of absorbing liquids such as water, urine, menstrual fluids, blood, wound exudates and the like.

DESCRIPTION OF THE PREFERRED EMBODIMENTS

In Example 1 which follows herein, the invention will be described in detail in connection with absorbent fibers and an amount of glyceryl monolaurate which is effective to inhibit the production of enterotoxins A, B, C or a combination of TSST-1 and A being produced by S. aureus bacteria when said bacteria are brought into contact with cotton fibers such as those used in catemenial products, e.g., tampons. It will be understood that the principles of the invention apply as well to other types of absorbent fibers as well as to absorbent products such as wound dressings, disposable diapers, sanitary napkins and other kinds of tampons, such as those intended for medical, surgical, dental and/or nasal use.

Cotton fibers were obtained from Barnhardt Manufacturing Company of Charlotte, N.C. The fibers were 100% cotton, such that the fibers were substantially free of all finishes and additives, such as surfactants and the like commonly used in commercial production. The cotton fibers were placed in a kier and heated with water to a temperature between about 190° and about 200° F. at which time both glyceryl monolaurate and sodium oleate (4:1 ratio concentration) were added to the water to form an emulsion in the kier. Varying concentrations of glyceryl monolaurate were added to the fibers, such that each set of fibers contained emulsions having 0.22%, 0.78%, 1.12% and 1.89% glyceryl monolaurate by weight. The kier was closed and pressurized to 10 lbs. The system was run for thirty minute cycles. After completion, the wet cotton fiber was centrifuged for five minutes and the fibers were dried in the oven at 250° F. with a 6.5 minute dwell time and subsequently carded using commercially available carding equipment into a fibrous web weighing about 33.6 g/m$^2$.

A sample of glyceryl monolaurate available under the tradename "Monomuls 90 L-12" was obtained from Henkel Corporation of Germany and found to contain 96% by weight of glyceryl monolaurate. No glyceryl dilaurate was detected. Glyceryl monolaurate is a GRAS compound listed by the FDA for use as a food emulsifier. This material is suggested for use in anti-caries products, insecticides, cosmetic preparations, and food compositions.

The following examples are illustrative of the effects of the absorbent products of this invention upon the production of enterotoxins A, B, C and TSST-1 with enterotoxin A. Of course, these examples merely illustrate the products of the invention without limiting the scope of the invention.

EXAMPLE 1

Uniformly coated cotton fibers which have been carded, containing, respectively, 0.22, 0.78, 1.12 and 1.89% w/w of the aforementioned glyceryl monolaurate based on the weight of the fiber, were weighed into 2.38-gram quantities in duplicate. The glyceryl monolaurate-treated fibers were then tested according to the Tampon Sac Method reported by Reiser et al. in the Journal of Clinical Microbiology Vol. 25, August 1987, pp. 1450–1452, the disclosure of which is hereby incorporated by reference. *Staphylococcus aureus* strain FRI-100, a known staphylococcal enterotoxin A producer, was used as the test organism in this Example. Strain FRI-100 originated as a food isolate from the Food Research Institute in Madison, Wis. Strain FRI-100 was obtained from Dr. Pat Schlievert, Dept. of Microbiology of the University of Minnesota Medical School, Minneapolis, Minn. A second strain of *S. aureus* obtained from Dr. Schlievert, designated Mn Hoch, was identified as an enterotoxin B-only producer. This strain was isolated from a nonmenstrual case of Toxic Shock Syndrome. A third strain of *S. aureus* provided by Dr. Schlievert as an enterotoxin C producer designated Mn Don was also isolated from a nonmenstrual case of Toxic Shock Syndrome. A fourth strain of *S. aureus* provided from Dr. Schlievert produces both TSST-1 and enterotoxin A designated Mn8. Control *S. aureus* isolates which do not produce any enterotoxins were used as controls in the assays.

*S. aureus* suspensions were separately prepared by thoroughly mixing one (1) milligram of the lyophilized *S. aureus* strain to one (1.0) milliliter of Brain Heart Infusion (BHI) Broth (obtained from Difco Laboratories, Detroit, Mich.) and transferring said mixture into a test tube containing five (5) milliliters of BHI Broth. The suspensions were thoroughly mixed again and incubated for 24 hours at 37° C. prior to use.

100 milliliters of brain heart infusion (BHI) agar (also obtained from Difco Laboratories in Detroit, Mich., U.S.A.) were put into each of ten 3.8 cm×20 cm culture tubes. Cellulose dialysis bags were made and sterilized in the manner reported by Reiser et al. The sterile cellulose sacs were inoculated with the aforementioned *S. aureus* suspension in an amount sufficient to provide at the beginning of the test a concentration therein of 1.9×10$^8$ CFU/ml *Staphylococcus aureus* bacteria.

A bundle of glyceryl monolaurate-treated cotton fibers weighing 2.38 grams was inserted into a sterile dialysis bag containing the *S. aureus* bacteria and each bag was then inserted into a culture tube containing the BHI agar. Two controls, each in duplicate, were used. In one control (called the "inoculum control"), an inoculated dialysis bag (with no fiber therein) was placed in each of two culture tubes containing BHI agar. In the second control, two untreated bundles weighing 2.38 g each (i.e. cotton fibers without finishes and the like exactly as the test fibers but not treated with glyceryl monolaurate) were placed in dialysis bags which in turn were placed in culture tubes containing BHI agar. Thus, twelve culture tubes were used in this test, four containing the aforementioned controls (two with untreated cotton fibers; two without fibers) and the others containing the aforementioned increasing concentrations of glyceryl monolaurate from 0.22 to 1.89% w/w on cotton fibers in duplicate.

The concentrations of *S. aureus* strain FRI-100 viable cells and enterotoxin A at the outset of the test (0 hours) and after incubation for 24 hours at 37° C. are shown in Table I.

TABLE 1

THE EFFECT OF GLYCERYL MONOLAURATE TREATED COTTON FIBERS ON ENTEROTOXIN A FORMATION BY AND GROWTH OF *STAPHYLOCOCCUS AUREUS* FRI-100

| SAMPLE | FINAL CONCENTRATION OF S. AUREUS (×10$^8$ CFU/ml) | FINAL CONCENTRATION OF S. AUREUS$^a$ (Log$_{10}$ CFU/ml) | FINAL AMOUNT Enterotoxin A$^{b,c}$ (ug) |
|---|---|---|---|
| No Fiber (Control) | 210 | 10.32 | 2.50 |
| Untreated Fiber (Control) | 480 | 10.68 | 3.48 |
| Treated Fiber (0.22% GML) | 18 | 9.25 | 0.029 |
| Treated Fiber (0.78% GML) | 2.0 | 8.30 | 0.075 |
| Treated Fiber (1.12% GML) | 12.8 | 9.10 | 0.052 |
| Treated Fiber (1.89% GML) | 4.0 | 8.60 | <0.005 |

$^a$ = Number of viable *S. aureus* cells expressed as log to base 10.
$^b$ = As determined by the ELISA method reported by Reiser et al. in Applied and Environmental Microbiology, December 1982, pp. 1349–1355.
$^c$ = Mean determination of duplicate samples.

The data in Table 1 show that glyceryl monolaurate has a significant impact on Enterotoxin A production comparable to its effect on TSST-1 production. The total cell counts reflect only a 1.0–2.0 log reduction in *S. aureus* cell number.

The data in Table 1 show that when *S. aureus* FRI-100 strain, which produces Enterotoxin A, is exposed to fibers coated with glyceryl monolaurate (0.22% w/w) there is a 99% reduction in Enterotoxin A formation. With fibers coated with 0.78% w/w glyceryl monolaurate, a 98% reduction was noted. In higher concentrations of glyceryl monolaurate, such as 1.12% and 1.89% w/w glyceryl monolaurate, 99% reductions in Enterotoxin A formation were noted. At the end of the incubation period (24 hours), the log concentration of S. aureus cells in the presence of control cotton fibers was 10.68; the log concentration of S. aureus cells in the presence of fiber containing 0.22% glyceryl monolaurate was 9.25 (13% less); the log concentration of S. aureus cells in the presence of cotton fibers containing 0.78% glyceryl monolaurate was 8.30 (22% less); the log concentration of S. aureus cells in the presence of cotton fibers containing 1.12% w/w glyceryl monolaurate was 9.10 (15% less); and the log concentration of S. aureus cells in the presence of cotton fibers containing 1.89% w/w glyceryl monolaurate was 8.60 (19% less). Thus, although the amount of toxin produced by the S. aureus cells was almost entirely eliminated, the glyceryl monolaurate-coated fibers did not substantially reduce the number of viable the S. aureus cells.

Further, a dose-response effect could be noted with glyceryl monolaurate with respect to the amount of toxin produced in that the greater the glyceryl monolaurate content, the lower the amount of toxin that is produced.

This same trend could not be discerned in this Example with regard to viable cell number.

EXAMPLE 2

A second experiment was conducted to evaluate the effect of glyceryl monolaurate on Enterotoxin B production by S. aureua strain Mn Hoch obtained from a nonmenstrual Toxic Shock Syndrome case. The microorganism was transferred, inoculated, and evaluated using the experimental procedure described and set forth in Example 1. The cotton fibers which were untreated, cotton fibers treated with 0.22%, 0.78%, 1.12% and 1.89% w/w glyceryl monolaurate were weighed to 2.38 gram quantities and inserted into dialysis bags previously inoculated with S. aureus strain Mn Hoch, and tested as described in Example 1. The treated cotton fibers, the untreated cotton fiber controls and duplicate inoculum controls were then all tested in duplicate as described in Example 1. The test results are reported in Table 2.

TABLE 2

THE EFFECT OF GLYCERYL MONOLAURATE ON ENTEROTOXIN B PRODUCTION BY *STAPHYLOCOCCUS AUREUS* Mn Hoch

| SAMPLE | FINAL CONCENTRATION OF S. AUREUS ($\times 10^8$ CFU/ml) | FINAL CONCENTRATION OF S. AUREUS$^a$ ($Log_{10}$ CFU/ml) | FINAL AMOUNT Enterotoxin B$^{b,c}$ (ug) |
|---|---|---|---|
| No fiber (Control) | 7.20 | 8.85 | 41.04 |
| Untreated Fiber (Control) | 16.21 | 9.21 | 117.46 |
| Treated Fiber (0.22% GML) | 2.39 | 8.38 | 5.77 |
| Treated Fiber (0.78% GML) | 10.00 | 9.00 | 2.17 |
| Treated Fiber (1.12% GML) | 0.81 | 7.91 | 0.93 |
| Treated Fiber (1.89% GML) | 0.48 | 7.69 | 0.45 |

$^a$ = Number of viable S. aureus cells expressed as log to base 10.
$^b$ = As determined by the ELISA method reported by Reiser et al. in Applied and Environmental Microbiology Dec. 1982, pp. 1349-1355.
$^c$ = Mean determination of duplicate samples.

The data in Table 2 show that S. aureus Mn Hoch produced significantly less Enterotoxin B (95% less than the untreated control) in the presence of glyceryl monolaurate (0.22% w/w) coated cotton fibers. Treated cotton fibers with glyceryl monolaurate concentrations of 0.78% w/w resulted in a 98% reduction in Enterotoxin B production while greater than 99% reductions were noted with fibers coated with 1.12 and 1.89% w/w glyceryl monolaurate. At the end of the incubation period (24 hours), the log concentration of S. aureus cells in the presence of control cotton fibers was 9.21; the log concentration of S. aureus cells in the presence of fibers containing 0.22% glyceryl monolaurate was 8.38 (9% less); the log concentration of S. aureus cells in the presence of cotton fibers containing 0.78% glyceryl monolaurate was 9.00 (2% less); the log concentration of S. aureus cells in the presence of cotton fibers containing 1.12% glyceryl monolaurate was 7.91 (14% less); and the log concentration of S. aureus cells in the presence of cotton fibers containing 1.89% w/w glyceryl monolaurate was 7.69 (16% less).

EXAMPLE 3

A third experiment was conducted to evaluate the effect of glyceryl monolaurate on Enterotoxin C production by S. aureus MN Don which is an Enterotoxin C-only producer obtained from an individual with nonmenstrual Toxic Shock Syndrome. The microorganism was transferred, inoculated and evaluated using th experimental procedure described and set forth in Example 1. The cotton fibers untreated, cotton fibers treated with 0.22%, 0.78%, 1.12% and 1.89% w/w glyceryl monolaurate were weighed to 2.38 gram quantities and inserted into dialysis bags inoculated with S. aureus strain Mn Don and tested as described in Example 1. The coated cotton fibers, the untreated cotton fiber controls, and duplicate inoculum controls were then all tested in duplicate as described in Example 1. The test results are reported in Table. 3.

TABLE 3

THE EFFECT OF GLYCERYL MONOLAURATE ON ENTEROTOXIN C PRODUCTION BY *STAPHYLOCOCCUS AUREUS* Mn Don

| SAMPLE | FINAL CONCENTRATION OF S. AUREUS ($\times 10^8$ CFU/ml) | FINAL CONCENTRATION OF S. AUREUS$^a$ ($Log_{10}$ CFU/ml) | FINAL AMOUNT Enterotoxin C$^{b,c}$ (ug) |
|---|---|---|---|
| No Fiber (Control) | 69.18 | 9.84 | 1.55 |
| Untreated Fiber (Control) | 17.78 | 9.25 | 32.27 |
| Treated Fiber (0.22% GML) | 3.80 | 8.58 | 1.52 |
| Treated Fiber (0.78% GML) | 10.47 | 9.02 | 0.16 |
| Treated Fiber (1.12% GML) | 4.16 | 8.62 | 0.02 |
| Treated Fiber (1.89% GML) | 0.33 | 7.52 | 0.14 |

$^a$ = Number of viable S. aureus cells expressed as log to base 10.
$^b$ = As determined by the ELISA method reported by Reiser et al. in Applied and Environmental Microbiology Dec. 1982, pp. 1349-1355.
$^c$ = Mean determination of duplicate samples.

The data reported in Table 3 show that S. aureus Mn Don produced significantly less Enterotoxin C (95% less than the untreated control) in the presence of glyceryl monolaurate (0.22% w/w) coated cotton fibers. Treated cotton fibers with glyceryl monolaurate concentrations of 0.78% w/w and greater resulted in 99% reductions in Enterotoxin C formed over that generated by the untreated control. The log concentrations of *S. aureus* Mn Don cells in the presence of control cotton fibers was 9.25; the log concentration of *S. aureus* cells in the presence of fibers containing 0.22% glyceryl monolaurate was 8.58 (7% less); the log concentration of *S. aureus* cells in the presence of cotton fibers containing 0.78% glyceryl monolaurate was 9.02 (2% less); the log concentration of *S. aureus* cells in the presence of cotton fibers containing 1.12% glyceryl monolaurate was 8.62 (6% less); and the log concentration of *S. aureus* cells in the presence of cotton fibers containing 1.89% w/w glyceryl monolaurate was 7.52 (19% less).

EXAMPLE 4

A fourth experiment was conducted to evaluate the effect of glyceryl monolaurate on both TSST-1 and Enterotoxin A produced together by *S. aureus* MnS, which is a known high TSST-1 producer which also produces Enterotoxin A in lesser quantities. This *S. aureus* Mn8 isolate was obtained from the tri-state study of an individual with Toxic Shock Syndrome. The microorganism was transferred, inoculated, and evaluated using the experimental procedure described and set forth in Example 1. The cotton fibers untreated, treated with 0.22%, 0.78%, 1.12% and 1.89% w/w glyceryl monolaurate were weighed to 2.38 gram quantities and inserted into dialysis bags inoculated with *S. aureus* strain Mn8 and tested as described in Example 1. The coated cotton fibers, the untreated cotton fiber controls, and duplicate inoculum controls were then all tested in duplicate as described in Example 1. The test results are reported in Table 3.

glyceryl monolaurate both resulted in a 99% reduction in both TSST-1 and Enterotoxin A formations. At the end of the incubation period (24hours) the log concentration of *S. aureus* cells in the presence of control cotton fibers was 8.68; the log concentration of *S. aureus* cells in the presence of fibers containing 0.22% w/w glyceryl monolaurate was 8.16 (6% less); the log concentration of *S. aureus* cells in the presence of cotton fibers containing 0.78% glyceryl monolaurate was 7.79 (10% less); the log concentration of *S. aureus* cells in the presence of cotton fibers containing 1.12% w/w glyceryl monolaurate was 8.56 (1% less); and the log concentration of *S. aureus* cells in the presence of cotton fibers containing 1.89% w/w glyceryl monolaurate was 8.62 (1% less).

As can be seen from the preceding Examples 1–4, cotton fibers have been treated with varying levels of glyceryl monolaurate, a commercially available mixture comprising 96% by weight glyceryl monolaurate and no glyceryl dilaurate. The data reported in Tables 1–4 show that, depending on the levels of glyceryl monolaurate in the fibers, *S. aureus* bacteria produce significantly less toxin, in other words, are inhibited from producing significant amounts of toxin when compared to the amounts of toxin produced, under the same experimental conditions, by *S. aureus* bacteria in the presence of control fibers containing no glyceryl monolaurate.

The effectiveness of glyceryl monolaurate with respect to toxin production should not be dependent upon the type of fiber substrate on which it is placed. It has been shown previously that Lauricidin and related analogs are effective in reducing TSST-1 toxin production in absorbent products when used on various substrates

TABLE 4

| | THE EFFECT OF GLYCERYL MONOLAURATE ON TSST-1 AND ENTEROTOXIN A PRODUCTION BY *STAPHYLOCOCCUS AUREUS* Mn8. | | | |
|---|---|---|---|---|
| SAMPLE | FINAL CONCENTRATION OF VIABLE *S. AUREUS* CELLS ($\times 10^8$ CFU/ml) | FINAL CONCENTRATION OF *S. AUREUS*$^a$ ($\text{Log}_{10}$ CFU/ml) | FINAL AMOUNT TSST-1$^{b-c}$ (ug) | FINAL AMOUNT Enterotoxin A$^{b,c}$ (ug) |
| No Fiber (Control) | 354.81 | 10.55 | 18.0 | 11.38 |
| Untreated (Control) | 4.78 | 8.68 | 31.62 | 14.14 |
| Treated Fiber (0.22% GML) | 1.44 | 8.16 | 7.58 | 1.35 |
| Treated Fiber (0.78% GML) | 0.61 | 7.79 | 0.93 | 0.50 |
| Treated Fiber (1.12% GML) | 3.63 | 8.56 | 0.41 | 0.19 |
| Treated Fiber (1.89% GML) | 4.16 | 8.62 | 0.13 | 0.12 |

$^a$ = Number of viable *S. aureus* cells expressed as log to base 10.
$^b$ = As determined by the ELISA method reported by Reiser et al. in Applied and Environmental Microbiology Dec. 1982, pp. 1349–1355.
$^c$ = Mean determination of duplicate samples.

The data in Table 4 show that *S. aureus* Mn8 produced significantly less TSST-1 and Enterotoxin A in the presence of glyceryl monolaurate treated fiber. After exposure to 0.22% w/w glyceryl monolaurate treated fiber, *S. aureus* Mn8 produced 7.58 ug of TSST-1 which is 76% less than that noted in the untreated fiber control. This same fiber treated (0.22% w/w glyceryl monolaurate) resulted in a 90% reduction in Enterotoxin A formation over that observed in the control. The cotton fiber treated with 0.78% w/w glyceryl monolaurate resulted in a 97% reduction in TSST-1 formation with a 96% reduction in Enterotoxin A formation. The fiber containing 1.12% and 1.89% w/w as set forth in copending United States patent applications Ser. No. 343,965 filed Apr. 27, 1989 and Ser. No. 316,742 filed Apr. 27, 1990, which are hereby incorporated herein by reference. Furthermore, although the examples set forth above contain fibers having a coating of about 0.22% w/w of glyceryl monolaurate, the active compound should be effective to prevent toxin formation at lower concentrations, e.g., at concentrations of at least about 0.1% w/w active compound.

EXAMPLE 5

An experiment was conducted by Dr. Patrick Schlievert of University of Minnesota to evaluate the effect of tampons treated with glyceryl monolaurate on streptococcal pyrogenic exotoxins types A and B. The microorganism used in this experiment was Group A streptococcus strain C203, which produces streptococcal pyrogenic exotoxins A and B. In this experiment, the Tampon Sac Method of Reiser et al. was used to determine the effect of the treated tampon on toxin production. Dialysis tubing was inoculated with $5 \times 10^6$ colony forming units (CFU) of the bacteria in a 1-ml volume (Brain Heart Infusion Broth) with or without o.b. brand vaginal tampons. The tampons used weighed 3 gm and contained either 1 ml glyceryl monolaurate (1.0% w/w) or tampons without glyceryl monolaurate. The inoculated dialysis tubings were submerged in 75 ml brain heart infusion agar and incubated for 24 hours at 37° C. at 7% $CO_2$. The samples were then diluted four-fold with respect to the amount of fluid absorbed over the 24 hour period and CFU and toxin concentrations were determined. Plate counts were used to determine CFU concentration and Western blot anaylsis to measure toxin. The lower limit of detection of toxin was 0.003 ug. The data obtained are summarized in Table 5.

The results demonstrate that toxin production was quite low in the presence of the untreated tampon, and was undetectable in the presence of the treated tampons. Cell viability was also significantly affected. It was determined that the presence of oxygen adsorbed to the fibers of the tampon, as well as exposure of the microorganism to atmospheric oxygen may have contributed to the lower levels of toxin production and reduced cell viability in the dialysis bags in which tampons were located. It was decided to provide an anaerobic environment for the organism in subsequent tests.

TABLE 5

THE EFFECT OF GLYCERYL MONOLAURATE TREATED TAMPONS ON GROWTH AND TOXIN PRODUCTION BY STREPTOCOCCUS

| Sample | CFU[a] | SPE Type (µg/ml) A | B |
|---|---|---|---|
| Control (no tampon) | $6.5 \pm 2.7 \times 10^8$ | 12.0 | 6.0 |
| ob | $7.5 \pm 4.0 \times 10^6$ | 0.12 | 0.06 |
| ob + 1% GML | <40 | N.D.[b] | N.D. |

[a]CFU/ml of fluid absorbed into sac. In the presence of a tampon an average of 2.0 ml was absorbed. In the absence less than 0.25 ml was absorbed.
[b]N.D. none detected

EXAMPLE 6

In this experiment, conducted by Dr. Patrick Schlievert, glyceryl monolaurate was added in varying concentrations to 50 ml brain heart infusion broths. These solutions were then inoculated with $1.0 \times 10^6$ CFU/ml of group A streptococcus C203 or S. aureus MnS, a known TSST-1 producer. Samples containing C203 were incubated at 37° C., for 12 hours, without shaking, so as to reduce oxygen exposure, in the presence of 7% $CO_2$. Samples containing Mn8 were incubated comparably except with shaking (at a rate of 200 RPM) and in a standard incubator. The results of this experiment are summarized in Table 6.

TABLE 6

THE EFFECT OF GLYCERYL MONOLAURATE ON BOTH CELL VIABILITY AND TOXIN PRODUCTION BY STREPTOCOCCUS C203 AND STAPHYLOCOCCUS AUREUS Mn8

| Sample | GML mg/100 ml broth | CFU | SPE type A | B | TSST-1 |
|---|---|---|---|---|---|
| C203 | 0 | $3.1 \times 10^8$ | 6.0 | 3.0 | |
| | 0.05 | $3.5 \times 10^8$ | 6.0 | 3.0 | |
| | 0.1 | $3.2 \times 10^8$ | 1.5 | 0.75 | |
| | 0.25 | $3.3 \times 10^8$ | N.D. | N.D. | |
| | 0.5 | $3.2 \times 10^8$ | N.D. | N.D. | |
| | 0.75 | $2.0 \times 10^8$ | N.D. | N.D. | |
| | 1.0 | $4.0 \times 10^7$ | N.D. | N.D. | |
| | 1.25 | $3.5 \times 10^6$ | N.D. | N.D. | |
| | 1.50 | 0 | N.D. | N.D. | |
| | 1.75 | 0 | N.D. | N.D. | |
| | 2.0 | 0 | N.D. | N.D. | |
| | 5.0 | 0 | N.D. | N.D. | |
| | 10.0 | 0 | N.D. | N.D. | |
| MN8 | 0 | $8.4 \times 10^9$ | | | 48 |
| | 0.05 | $9.0 \times 10^9$ | | | 48 |
| | 0.1 | $9.4 \times 10^9$ | | | 48 |
| | 0.25 | $6.2 \times 10^9$ | | | 12 |
| | 0.5 | $1.8 \times 10^{10}$ | | | N.D. |
| | .75 | $9.7 \times 10^9$ | | | N.D. |
| | 1.0 | $2.1 \times 10^{10}$ | | | N.D. |
| | 1.25 | $7.0 \times 10^9$ | | | N.D. |
| | 1.5 | $1.4 \times 10^{10}$ | | | N.D. |
| | 1.75 | $1.1 \times 10^{10}$ | | | N.D. |
| | 2.0 | $4.0 \times 10^5$ | | | N.D. |
| | 2.25 | $2.0 \times 10^5$ | | | N.D. |
| | 2.5 | $2.3 \times 10^4$ | | | N.D. |
| | 5.0 | $2.1 \times 10^4$ | | | N.D. |
| | 10.0 | $2.9 \times 10^4$ | | | N.D. |

EXAMPLE 7

In this example, conducted by Dr. Patrick Schlievert, group A streptococcal strains, individually expressing SPEA, SPEB or SPEC and strains from groups B, F and G streptococci were evaluated for the effect of glyceryl monolaurate on their production of exotoxin. Using the method set forth in Example 6, organisms were exposed to varying concentrations of glyceryl monolaurate in a brain heart infusion broth. Strain 594, which produces SPEA, Strain 86-858, which produces SPEB, and Strain T18P, which produces SPEC toxins respectively, were used. Toxin production was measured by Western immunoblotting specific periods within 96 hours. The results of this experiment to determine the effect of glyceryl monolaurate on production of SPEA, SPEB and SPEC toxins are set forth in Table 7.

S. aureus strain Mn8 was also exposed to glyceryl monolaurate. The amount of TSST-1 production of S. aureus strain Mn8 was measured. The results of this test are set forth in Table 8.

Streptolysins O and S, also produced by strains 594, 86-858 and T18P, as well as Group B streptococcal hemolysin, Group F streptococcal hemolysin and Group G streptococcal hemolysin were measured by lysis of 0.1% sheep erythrocytes and 0.014% 2-mercaptoethanol as a reducing agent performed in 0.75% agarose in phosphate buffer solution (PBS), 4.5 ml/slide. The PBS was composed of 0.005 Molar sodium phosphate, 0.15 Molar NaCl, at pH 7.0. Hemolysis induced by 20 ul cell free culture added to wells punched in slides after 24 hours was used as a measure of hemolysin production. Lipase was measured in the same way as hemolysin, except that clearing of 0.1% tributyrin was used as the standard.

Results of reduced streptolysin O and S are also set forth in Table 7. The results of the experiments exploring the effect of glyceryl monolaurate on toxin production by Groups B, F and G streptococci are set forth in Tables 9, 10 and 11, respectively. The data demonstrate a marked reduction in the amounts of toxin and/or hemolysin produced by Groups A, B, F and G streptococci in the presence of glyceryl monolaurate.

TABLE 7

EFFECT OF GLYCERYL MONOLAURATE ON GROUP A STREPTOCOCCI

| Bacterium[a] | GML (μg/ml) | Log CFU/ml | SPE (μg/ml) | Reduced Hemolysin[b] |
|---|---|---|---|---|
| 594 (SPEA) | 0 | 8.6 | 3.2 | 7.0 |
| | 2.5 | 8.5 | 0.3 | 4.0 |
| | 10.0 | 8.3 | 0.3 | 0.0 |
| | 20.0 | 6.0 | 0.0 | 0.0 |
| 86-858 (SPEB) | 0 | 8.0 | 0.8 | 4.0 |
| | 2.5 | 7.7 | 0.0 | 2.0 |
| | 10.0 | 7.7 | 0.0 | 0.0 |
| | 20.0 | 5.8 | 0.0 | 0.0 |
| T18P (SPEC) | 0 | 7.9 | 0.4 | 8.0 |
| | 2.5 | 7.9 | 0.0 | 8.0 |
| | 10.0 | 6.1 | 0.0 | 0.0 |

[a] Inoculum size between $10^5$ and $10^6$ CFU/ml
[b] Includes streptolysin O and S measured in mm diameter of lysis

TABLE 8

EFFECT OF GML ON *Staphylococcus aureus*[a] MN8

| GML (μg/ml) | 4 hr | | | | 8 hr | | | | 24 hr | | | | 48 hr | | | | 96 hr | | | |
|---|---|---|---|---|---|---|---|---|---|---|---|---|---|---|---|---|---|---|---|---|
| | Log cells ml | L[b] | H[c] | T[d] | Log cells ml | L | H | T | Log cells ml | L | H | T | Log cells ml | L | H | T | Log cells ml | L | H | T |
| 0 | 6.8 | 2 | 0 | 0 | 9.0 | 10 | 9 | 2 | 10.2 | 15 | 15 | 40 | 10.2 | 15 | 15 | 40 | 10.3 | 15 | 16 | 40 |
| 20 | 5.8 | 2 | 0 | 0 | 7.5 | 6 | 0 | 0 | 10.0 | 15 | 13 | 16 | 10.3 | 14 | 15 | 40 | 10.3 | 15 | 16 | 40 |
| 100 | 5.8 | 2 | 0 | 0 | 6.3 | 6 | 0 | 0 | 8.3 | 8 | 0 | 0 | 10.0 | 13 | 4 | 8 | 10.3 | 15 | 8 | 16 |
| 300 | 5.6 | 2 | 0 | 0 | 5.8 | 2 | 0 | 0 | 6.9 | 4 | 0 | 0 | 7.0 | 6 | 0 | 0 | 10.3 | 15 | 2 | 8 |

[a] Inoculum size 1.0 × $10^5$/ml
[b] L, Lipase mm
[c] H, Hemolysin mm lysis Rabbit RBC
[d] T, TSST-1 (μg/ml)

TABLE 9

EFFECT OF GML ON GROUP B STREPTOCOCCUS

| GML (μg/ml) | 8 hr | | 24 hr | |
|---|---|---|---|---|
| | Log cell/ml | Hemolysin | Log cell/ml | Hemolysin |
| 0 | 8.7 | 2 | 8.5 | 2 |
| 2.5 | 8.1 | 0 | 8.4 | 0 |
| 10.0 | <4.0 | 0 | <3.0 | 0 |

Inoculum size 2.0 × $10^5$/ml

TABLE 10

EFFECT OF GML ON GROUP F STREPTOCOCCUS

| GML (μg/ml) | 8 hr | | 24 hr | |
|---|---|---|---|---|
| | Log cells/ml | Hemolysin | Log cells/ml | Hemolysin |
| 0 | 8.3 | 7 | 8.3 | 7 |
| 2.5 | 8.5 | 0 | 8.3 | 0 |
| 10.0 | <$10^4$ | 0 | <$10^3$ | 0 |

Inoculum size 2.0 × $10^5$/ml

TABLE 11

EFFECT OF GML ON GROUP G STREPTOCOCCUS

| GML (μg/ml) | 8 hr | | 24 hr | |
|---|---|---|---|---|
| | Log cell/ml | Hemolysin | Log cell/ml | Hemolysin |
| 0 | 8.9 | 8 | 10.0 | 8 |
| 2.5 | 8.1 | 5 | 10.0 | 6 |
| 10.0 | <$10^4$ | 0 | <$10^3$ | 0 |

Inoculum size 8 × $10^5$/ml

EXAMPLE 8

In this experiment, conducted by Dr. Patrick Schlievert, attempts were made to induce streptococcal strain C203 and staphylococcal strain Mn8 to grow on plates containing glyceryl monolaurate. The minimum inhibitory concentration of glyceryl monolaurate for strain C203 was 1 mg/100 ml on the agar plates when 5×$10^6$ CFU were plated. The 2 mg/100 ml plate cont growth. The minimum inhibitory concentration of glyceryl monolaurate for strain Mn8 was 5 mg/100 ml when 7×$10^8$ CFU were plated. The 7.5 mg/100 ml plate contained no growth. This experiment was attempted on an average of twice per week for a period of six months. The date indicate that no mutants able to grow in the presence of previously inhibitory levels of glyceryl monolaurate.

EXAMPLE 9

Predictive Example

In this experiment, the methods of Examples 5-7 to test the effectiveness of glyceryl monolaurate and related analogous compounds should be used. However, the tampons should be subjected to an anaerobic chamber in order to expunge all oxygen adsorbed to the fibers. The tampons with and without glyceryl monolaurate as well as the control samples should be inserted into the dialysis bags under anaerobic conditions and incubated in an anaerobic and/or reduced oxygen chamber so as to minimize the exposure of the streptococcus organisms to atmospheric and/or adsorbed oxygen. At various intervals, the toxin levels produced by the microorganisms should be evaluated. It is expected, based upon the other examples herein, that the glyceryl monolaurate and other analogous compounds will effectively inhibit the production of streptococcal pyrogenic exotoxins and hemolysins by Groups A, B, F and G streptococci without substantially inhibiting cell growth.

What is claimed is:
1. A method of inhibiting the production of Enterotoxin A, Enterotoxin B or Enterotoxin C comprising exposing an absorbent product to Enterotoxin A-pro- ducing *Staphylococcus aureus* bacteria, Enterotoxin B-producing *Staphylococcus aureus* bacteria, or Enterotoxin C-producing *Staphylococcus aureus* bacteria, wherein said absorbent product comprises an effective Enterotoxin-inhibiting amount of a compound selected from the group consisting of:

a) monoesters of a polyhydric aliphatic alcohol and a fatty acid containing from eight to eighteen carbon atoms and wherein said monoester has at least one hydroxyl group associated with its aliphatic alcohol residue;

b) diesters of a polyhydric aliphatic alcohol and a fatty acid containing from eight to eighteen carbon atoms and wherein said diester has at least one hydroxyl group associated with its aliphatic alcohol residue; and c) mixtures of said monoesters and diesters, and wherein said Enterotoxin A, Enterotoxin B or Enterotoxin C-producing *Staphylococcus aureus* bacteria contacts said compound.

2. A method according to claim 2 wherein said absorbent product is a catemenial tampon.

3. A method according to claim 1 wherein said fatty acid is lauric acid.

4. A method of inhibiting the production of Streptococcal pyrogenic exotoxins A, B or C, streptococcal hemolysins produced by Groups A, B, F or G streptococci comprising exposing an absorbent product to said Group A, B, F or G streptococci wherein said absorbent product comprises a compound selected from the group consisting of:

a) monoesters of a polyhydric aliphatic alcohol and a fatty acid containing from eight to eighteen carbon atoms and wherein said monoester has at least one hydroxyl group associated with its aliphatic alcohol residue;

b) diesters of a polyhydric aliphatic alcohol and a fatty acid containing from eight to eighteen carbon atoms and wherein said diester has at least one hydroxyl group associated with its aliphatic alcohol residue; and c) mixtures of said monoesters and diesters, and wherein said SPEA, SPEB, SPEC, or hemolysins-producing streptococcal bacteria contact said compound.

5. A method according to claim 1 wherein said polyhydric alcohol is glycerol.

6. A method according to claim 1 wherein said compound is glyceryl monolaurate.

7. A method according to claim 1 wherein said absorbent product is gauze material.

8. A method according to claim 1 wherein said absorbent product is nasal packing.

9. A method of inhibiting the production of Streptococcal pyrogenic exotoxins A, B or C, streptococcal hemolysins produced by Groups A, B, F or G streptococci comprising exposing a composition to said Group A, B, F or G streptococci, wherein said composition comprises a pharmaceutically acceptable carrier and a compound selected from the group consisting of:

a) monoesters of a polyhydric aliphatic alcohol and a fatty acid containing from eight to eighteen carbon atoms and wherein said monoester has at least one hydroxyl group associated with its aliphatic alcohol residue;

b) diesters of a polyhydric aliphatic alcohol and a fatty acid containing from eight to eighteen carbon atoms and wherein said diester has at least one hydroxyl group associated with its aliphatic alcohol residue; and c) mixtures of said monoesters and diesters, and wherein said SPEA, SPEB, SPEC, or hemolysins-producing bacteria contact said compound.

* * * * *